(12) United States Patent
Almog et al.

(10) Patent No.: US 9,784,689 B2
(45) Date of Patent: Oct. 10, 2017

(54) METHOD AND SYSTEM FOR INSPECTING AN OBJECT WITH AN ARRAY OF BEAMS

(71) Applicant: APPLIED MATERIALS ISRAEL LTD., Rehovot (IL)

(72) Inventors: Ido Almog, Rehovot (IL); Ron Naftali, Shoham (IL)

(73) Assignee: APPLIED MATERIALS ISRAEL LTD., Rehovot (IL)

( * ) Notice: Subject to any disclaimer, the term of this patent is extended or adjusted under 35 U.S.C. 154(b) by 47 days.

(21) Appl. No.: 14/797,040

(22) Filed: Jul. 10, 2015

(65) Prior Publication Data
US 2017/0010219 A1    Jan. 12, 2017

(51) Int. Cl.
*G01N 21/00* (2006.01)
*G01N 21/88* (2006.01)
*G01N 21/95* (2006.01)

(52) U.S. Cl.
CPC ..... *G01N 21/8806* (2013.01); *G01N 21/9501* (2013.01); *G01N 2201/0638* (2013.01)

(58) Field of Classification Search
CPC ............... G01N 21/8806; G01N 21/47; G01N 21/8851; G01N 21/9501; G01N 21/95607; G02B 21/14
USPC .............................. 356/237.1–237.5; 348/131
See application file for complete search history.

(56) References Cited

U.S. PATENT DOCUMENTS

| | | | | |
|---|---|---|---|---|
| 6,809,808 B2* | 10/2004 | Feldman | ............ | G01N 21/8806 356/237.1 |
| 6,943,898 B2* | 9/2005 | Libinson | ................ | G02B 21/14 356/516 |
| 7,002,695 B2* | 2/2006 | Feldman | .......... | G01N 21/95607 356/516 |
| 7,053,395 B2 | 5/2006 | Feldman et al. | | |

(Continued)

OTHER PUBLICATIONS

U.S. Appl. No. 14/800,625, "Notice of Allowance", Aug. 24, 2016, 8 pages.

*Primary Examiner* — Hoa Pham
(74) *Attorney, Agent, or Firm* — Kilpatrick Townsend & Stockton LLP (57) ABSTRACT

According to an embodiment of the invention there may be provided a system for inspecting an object, the system may include a traveling lens acousto-optic device that is configured to generate a sequence of traveling lenses that propagate through an active region of the traveling lens acousto-optic device; an illumination unit that that is configured to illuminate the sequence of traveling lenses to provide a sequence of input beams; a first beam splitter that is configured to split the sequence of input beams to an intermediate array of intermediate beams, the intermediate array comprises multiple sequences of intermediate beams, the sequences of intermediate beams are spaced apart from each other; a masking unit that is configured to mask first beams of the intermediate array and unmask output beams of the intermediate array in an alternating manner; multiple detectors; and an objective lens that is configured to receive the output beams, direct the output beams towards multiple (Continued)

areas of the object, receive collected beams from the multiple areas of the object, and direct the collected beams towards the multiple detectors; and wherein each detector is associated with an area of the multiple areas.

14 Claims, 9 Drawing Sheets

(56) References Cited

U.S. PATENT DOCUMENTS

| | | | |
|---|---|---|---|
| 8,488,117 B2* | 7/2013 | Feldman | G01N 21/8806 356/237.2 |
| 8,659,754 B2* | 2/2014 | Feldman | G01N 21/8806 356/237.2 |
| 9,535,014 B1* | 1/2017 | Feldman | G01N 21/9501 |
| 2007/0109546 A1* | 5/2007 | Meshulach | G01N 21/21 356/445 |
| 2008/0100830 A1* | 5/2008 | Veis | G01N 21/8851 356/237.1 |
| 2012/0086937 A1 | 4/2012 | Feldman et al. | |
| 2013/0286191 A1* | 10/2013 | Ito | G01N 21/47 348/131 |

\* cited by examiner

METHOD AND SYSTEM FOR INSPECTING AN OBJECT WITH AN ARRAY OF BEAMS

BACKGROUND OF THE INVENTION

A variety of systems are used for automated inspection of semiconductor wafers, in order to detect defects, particles and/or patterns on the wafer surface as part of a quality assurance process in semiconductor manufacturing processes. It is a goal of current inspection systems to have high resolution and high contrast imaging in order to provide the reliability and accuracy demanded in sub-micron semiconductor manufacturing processes. However, it is also important to have a high-speed process that permits a large volume throughput so that the quality and assurance processes do not become a bottleneck in the wafer production process. Accordingly, the optical inspection systems must use shorter wave lengths, higher numerical aperture optics and high density image capture technology in order to enable the processing of data from such systems at sufficiently high rates that will satisfy the desired product throughput requirements.

A conventional imaging architecture that is used in wafer inspection systems at this time utilizes a single spot scanning laser for high-speed imaging. However, the data rates achievable by such architectures are limited by the physical constraints that arise due to limitations in the speed and quality of the single laser beam, the applicable optical system and related detection devices. For example, the single laser acting as a point light source is focused as a spot onto the object under inspection and is scanned across the surface of the object, which may be stationary or moved on a stage mechanism in coordination with the scan. The reflected light from the object is then imaged onto a detector, which generates pixel data from the scanning process.

The detector may be a photo multiplier detector (PMT) or a CCD array, whose individual elements are positioned to receive the reflected light as the beam is scanned and be read our serially, in a conventional fashion. While a high resolution may be obtained from such point source illumination, the requirement to scan each point in the field in order to construct a viewable image subjects the system to a limitation on its throughput.

The scanning of the single laser beam may be accomplished by a rotating mirror system, as seen in U.S. Pat. No. 5,065,008 or an acousto-optic cell. However, these single spot scanning architecture necessarily have a limited speed and are possibly subject to scan aberrations, low illumination brightness and potential thermal damage to the object when high brightness laser sources are used. The high data rates required to inspect the submicron structures of current semiconductor products cannot be achieved, even when a stage-type scanning system is used that moves the object relative to a fixed illumination and image location while a synchronized scanning pattern is produced by moving the single point of light over an area at the fixed location.

One way to increase the throughput of the inspection is to scan the object with set of laser beams ordered in a single or multiple lines which are scanning collinearly in a direction parallel to the line. This solution suffers from cross-talk between adjacent beams of the same line.

Accordingly, there is a need for an object scanning system that will improve object throughput, while maintaining or even improving the reliability and accuracy of the data collected during the scan of an object, whether in a stationary or stage-type system.

BRIEF SUMMARY OF THE INVENTION

According to an embodiment of the invention there may be provided a system for inspecting an object, the system may include a traveling lens acousto-optic device that may be configured to generate a sequence of traveling lenses that propagate through an active region of the traveling lens acousto-optic device; an illumination unit that that may be configured to illuminate the sequence of traveling lenses to provide a sequence of input beams; a first beam splitter that may be configured to split the sequence of input beams to an intermediate array of intermediate beams, the intermediate array may include multiple sequences of intermediate beams, the sequences of intermediate beams are spaced apart from each other; a masking unit that may be configured to mask first beams of the intermediate array and unmask output beams of the intermediate array in an alternating manner; multiple detectors; and optics that are configured to receive the output beams, direct the output beams towards multiple areas of the object, receive collected beams from the multiple areas of the object, and direct the collected beams towards the multiple detectors; and wherein each detector may be associated with an area of the multiple areas.

The output beams may form a second array that may be oriented in relation to the intermediate array.

The number of first beams may be one half of a number of the intermediate beams of the intermediate array.

The number of first beams may exceed one half of a number of the intermediate beams of the intermediate array.

The masking unit may include a plurality of apertures, wherein each aperture corresponds to a scan pattern of a single output beam.

The masking unit may include a plurality of apertures that are arranged in a diagonal manner.

The at least two sequences of intermediate beams of the multiple sequences of intermediate beams may be parallel to each other.

The at least two sequences of intermediate beams of the multiple sequences of intermediate beams may not be parallel to each other.

According to an embodiment of the invention there may be provided a method for inspecting an object, the method may include generating, by a traveling lens acousto-optic device, a sequence of traveling lenses that propagate through an active region of the traveling lens acousto-optic device; illuminating, by an illumination unit, the sequence of traveling lenses to provide a sequence of input beams; splitting, by a first beam splitter, the sequence of input beams to an intermediate array of intermediate beams, the intermediate array may include multiple sequences of intermediate beams, the sequences of intermediate beams are spaced apart from each other; masking, by a masking unit, mask first beams of the intermediate array and unmasking output beams of the intermediate array in an alternating manner; receiving, by optics, the output beams; directing, by the optics, the output beams towards multiple areas of the object; receiving collected beams from the multiple areas of the object; and directing the collected beams towards multiple detectors; and wherein each detector may be associated with an area of the multiple areas.

The output beams may form a second array that may be oriented in relation to the intermediate array.

According to an embodiment of the invention there may be provided a system for inspecting an object, the system may include a traveling lens acousto-optic device adapted to generate a traveling lens that propagates through an active region of the traveling lens acousto-optic device; an illumination unit that that may be configured to illuminate a first portion of the active region to provide an input beam that propagates along an input scan axis; an input beam splitter that may be configured to split the input beam to an output array of output beams that may include rows of output beams and columns of output beams; wherein the output beams propagate along an output scan axis that may be oriented to the columns of the output beams; multiple detectors; and optics that may be configured to receive the output beams, direct the output beams towards multiple areas of the object, receive collected beams from the multiple areas of the object, and direct the collected beams towards the multiple detectors; and wherein each detector may be associated with an area of the multiple areas.

The output scan axis may be oriented by forty five degrees in relation to the columns of the output beams.

The output scan axis may be oriented by an angle that differs from forty five degrees in relation to the columns of the output beams.

The number of the rows of output beams may differ from a number of the columns of output beams.

The number of the rows of output beams may equal a number of the columns of output beams.

According to an embodiment of the invention there may be provided a method for inspecting an object, the method may include: generating, by a traveling lens acousto-optic device, a traveling lens that propagates through an active region of the traveling lens acousto-optic device; illuminating, by an illumination unit, a first portion of the active region to provide an input beam that propagates along an input scan axis; splitting, by an input beam splitter, the input beam to an output array of output beams that may include rows of output beams and columns of output beams; wherein the output beams propagate along an output scan axis that may be oriented to the columns of the output beams; receiving, by optics, the output beams; directing, by the optics, the output beams towards multiple areas of the object; receiving collected beams from the multiple areas of the object; and directing the collected beams towards multiple detectors; and wherein each detector may be associated with an area of the multiple areas.

BRIEF DESCRIPTION OF THE DRAWINGS

The subject matter regarded as the invention is particularly pointed out and distinctly claimed in the concluding portion of the specification. The invention, however, both as to organization and method of operation, together with objects, features, and advantages thereof, may best be understood by reference to the following detailed description when read with the accompanying drawings in which:

It will be appreciated that for simplicity and clarity of illustration, elements shown in the figures have not necessarily been drawn to scale. For example, the dimensions of some of the elements may be exaggerated relative to other elements for clarity. Further, where considered appropriate, reference numerals may be repeated among the figures to indicate corresponding or analogous elements.

DETAILED DESCRIPTION OF THE DRAWINGS

In the following detailed description, numerous specific details are set forth in order to provide a thorough understanding of the invention. However, it will be understood by those skilled in the art that the present invention may be practiced without these specific details. In other instances, well-known methods, procedures, and components have not been described in detail so as not to obscure the present invention.

The subject matter regarded as the invention is particularly pointed out and distinctly claimed in the concluding portion of the specification. The invention, however, both as to organization and method of operation, together with objects, features, and advantages thereof, may best be understood by reference to the following detailed description when read with the accompanying drawings.

It will be appreciated that for simplicity and clarity of illustration, elements shown in the figures have not necessarily been drawn to scale. For example, the dimensions of some of the elements may be exaggerated relative to other elements for clarity. Further, where considered appropriate, reference numerals may be repeated among the figures to indicate corresponding or analogous elements.

Because the illustrated embodiments of the present invention may for the most part, be implemented using electronic components and circuits known to those skilled in the art, details will not be explained in any greater extent than that considered necessary as illustrated above, for the understanding and appreciation of the underlying concepts of the present invention and in order not to obfuscate or distract from the teachings of the present invention.

Any reference in the specification to a method should be applied mutatis mutandis to a system capable of executing the method and should be applied mutatis mutandis to a non-transitory computer readable medium that stores instructions that once executed by a computer result in the execution of the method.

Any reference in the specification to a system should be applied mutatis mutandis to a method that may be executed by the system and should be applied mutatis mutandis to a non-transitory computer readable medium that stores instructions that may be executed by the system.

Any reference in the specification to a non-transitory computer readable medium should be applied mutatis mutandis to a system capable of executing the instructions stored in the non-transitory computer readable medium and should be applied mutatis mutandis to method that may be executed by a computer that reads the instructions stored in the non-transitory computer readable medium.

The following detailed description is of exemplary embodiments of the invention but the invention is not limited thereto, as modifications and supplemental structures may be added, as would be apparent to those skilled in the art. In particular, but without limitation, while an exemplary embodiment may be disclosed with regard to the inspection of a subject surface by detecting reflected light using a light source and detecting unit that are disposed on a common side of an object (a "reflective system"), it would be readily apparent to one skilled in the art that the teachings are readily adaptable to the inspection of an object by detecting transmitted light with a detecting unit that is on a side of an object opposite to that of the light source (a "transmissive system").

While the reflective system and the transmissive system differ, for one example by the absence of a beam splitter in the transmissive system, the principles of the present invention are applicable to both types of systems. As would be understood by one skilled in the art, both types of systems may be utilized separately or together in the inspection of an object, in accordance with the present invention.

Figure 1A:
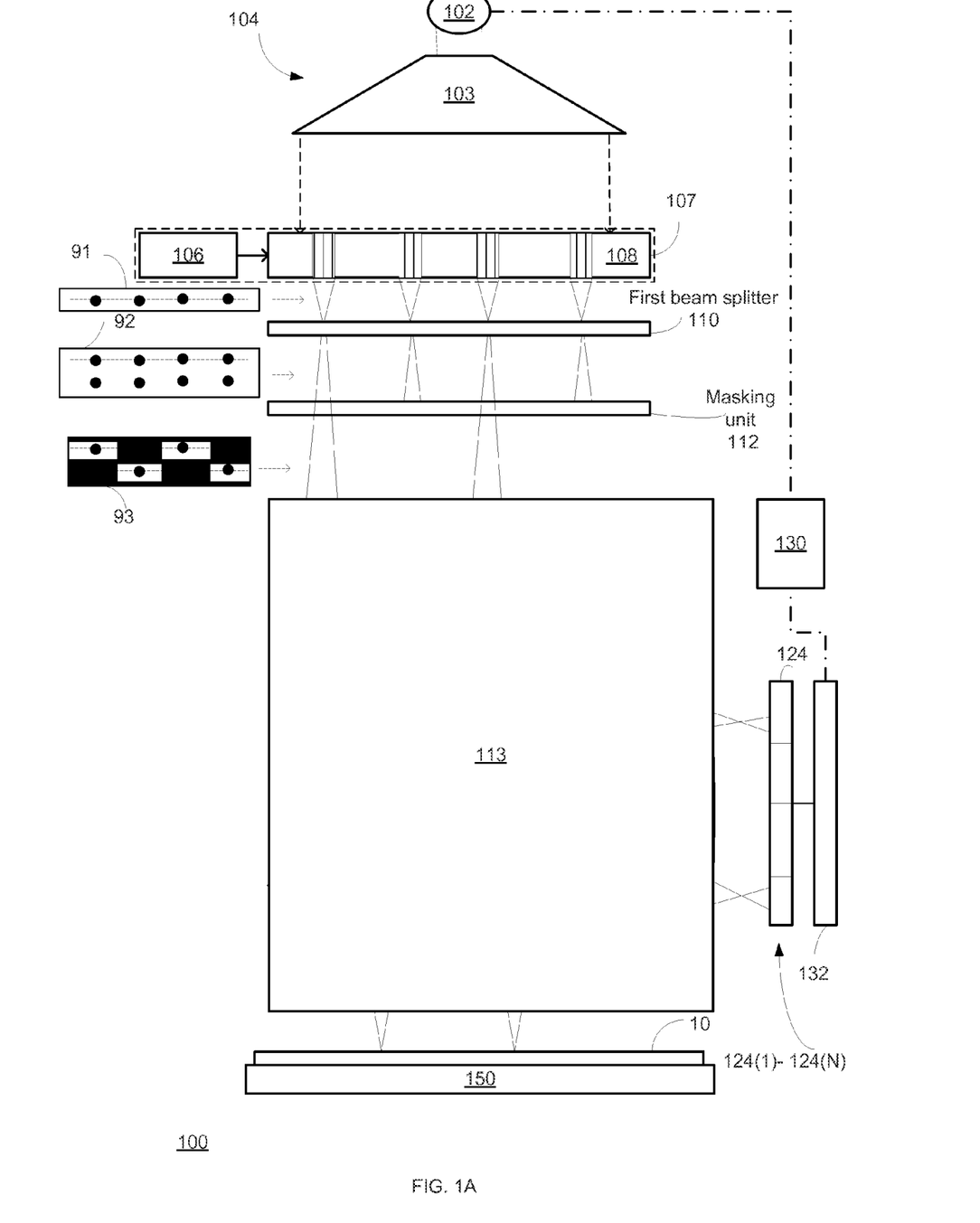
FIG. 1A illustrates a system and an object according to an embodiment of the invention.

FIG. 1A illustrates a system 100 and object 10 according to an embodiment of the invention.

Without limitation and only by example, object 10 may be any semiconductor product having multiple semiconductor devices thereon, at any of several stages of manufacture, or may be a mask, reticule or the like used in a manufacturing process, where such object must be inspected for defects, foreign objects or pattern accuracy. It is desirable in such systems to identify with high accuracy and reliability the size, location and type of structure, defect or object that appears on the object surface. It also is desirable to undertake such identification at high speed, in order to minimize the delay in the manufacturing process that is provided to the inspection and quality assurance steps.

System 100 is illustrated as including: (a) illumination unit 104 that includes light source 102 and beam expander 103 for expanding light from the light source 102, (b) traveling lens acousto-optic device 107 that includes transducer 106 and Bragg cell 108 that acts as the active region of the traveling lens acousto-optic device, (c) first beam splitter 110, (d) masking unit 112, (e) optics 113, (f) detection unit 124 that includes a plurality of detectors 124(1)-124(N), N being a positive integer, (g) image processor 132, (h) controller 130, and (i) a mechanical stage 150 for supporting and moving object 10.

Controller 130 is configured to control the operation of system 100.

Light source 102 is adapted to generate a beam of light such as but not limited to coherent light. It is noted that the term light refers to electromagnetic radiation at the visible range as well as ultraviolet, deep ultra violet and extreme deep ultra violet radiation. For wafer inspection, the light source preferably operates at a short wavelength, for example, 248 nm or 193 nm, in order to produce high resolution, with stable output power (or stable pulse energy and pulse rate), a stable transverse mode and a stable beam pointing.

Beam expander 103 expands the light beam in order to illuminate a predetermined part of Bragg cell 108. The predetermined part may be the majority of the Bragg cell, the entire Bragg cell or less than the majority of the Bragg cell. The predefined part should be large enough to enable a sequence of beams generated by a sequence of traveling lens within the Bragg cell to complete a predefined scan pattern.

Traveling lens acousto-optic device 107 is configured to generate a sequence of traveling lenses that propagate through Bragg cell 108. FIG. 1A illustrates four traveling lenses but the number of travelling lenses may differ from four.

It is noted that once a sequence of travelling lenses completes a predefined scan pattern a new sequence travelling lens is generated.

The traveling lens acousto-optic device 107 can resemble the traveling lens of acousto-optic device illustrated in U.S. Pat. Nos. 6,809,808, 7,053,395, 6,943,898, 6,853,475, 7,528,940, and 7,002,695—all being incorporated herein by reference.

The Bragg cell 108 may include a single crystal that is effective to generate one or more traveling lenses in response to one or more radio frequency chirps.

The single crystal in the device may be composed of a material that is compatible with an ultraviolet (UV) light source, preferably having an acousto-optic medium made of fused silica, GaAs or TeO$_2$ glass, although other known materials having UV compatibility, may be used. The crystal may have an anti-reflective coating on each major side that rated at less than 0.5% for both sides. The traveling lens acousto-optic device may operate in a longitudinal acoustic mode at a wavelength of 266 nm and at a center frequency of 200 MHz with a bandwidth of 130 MHz. RF power may be less than 3.0 watts. The active aperture of the device may be 1.0 mm "H" by 60 mm "L" in one exemplary embodiment.

Illumination unit 140 is configured to illuminate the sequence of traveling lenses to provide a sequence of input beams. Box 91 illustrates four input beams. Each time a new sequence of travelling lenses is generate a new sequence of input beam is created.

The sequence of input beams propagates towards first beam splitter 110. First beam splitter 110 splits the sequence of input beams to an intermediate array 92 of intermediate beams. First beam splitter 110 may include one or more gratings such as one or more Damman gratings.

The intermediate array 92 includes multiple intermediate sequences, each intermediate sequence includes a sequence of intermediate beams. The intermediate sequences are spaced apart from each other. In FIG. 1 the intermediate array 92 includes two intermediate sequences that are parallel to each other and each intermediate sequence includes four intermediate beams.

It is noted that the intermediate array 92 may include more than two intermediate sequences. It is further noted that two or more intermediate sequences of the intermediate array 92 may not be parallel to each other.

The intermediate array 92 propagates towards masking unit 112.

Masking unit 112 is configured to partially mask the traveling beams along the two scan lines. A typical scheme optimized for cross talk reduction may consist of unmasked areas configured in an alternating manner. Since each unmasked area typically imaged on a single detector—the output beams will not include a pair of adjacent beams that belong to the same sequence of beams of the intermediate array 92.

Box 93 illustrates masking unit 112 and output beams that propagate through apertures of the masking unit 112.

The output beams propagate towards optics 113. Optics 113 is configured to receive the output beams, direct the output beams towards multiple areas of the object 10, receive collected beams from the multiple areas of the object 10, and direct the collected beams towards the multiple detectors of detection unit 124 out of the plurality of detectors 124(1)-124(N). Each of the multiple detectors is associated with an area of the multiple areas. The multiple detectors may form a subset of the plurality of detectors 124(1)-124(N).

Multiple detectors of detection unit 124 detect light from the multiple illuminated areas of object 10. They generate detection signals that can be stored and later on processed (for example by image processor 132) in order to detect defects.

Detect detection methods such as die to die comparison, die to golden die comparison, die to design rule comparison are known in the art and require no additional explanation. The inventors used non-imaging detectors but this is not necessarily so imaging detectors can be used, especially when the collection path is designed such as to image the illuminated areas of object 10 onto the detectors. It is noted that a CCD array or another detector array can be regarded as multiple detectors.

It is noted that although FIG. 1A illustrates bright field illumination and collection that system 100 can apply dark field illumination and collection as well as a combination of dark field and bright field techniques, as illustrated in U.S. Pat. No. 6,853,475 of Feldman et al., which is incorporated herein by reference.

Mechanical stage 150 supports and moves object 10 along a mechanical movement direction that is traverse (and even perpendicular) to a scan direction of the output beams. It is noted that system 100 can also move optics 113 while maintaining object 10 at the same position. Alternatively, both optics and sample can be mechanically transferred. Yet according to an embodiment of the invention the object 10 is rotated by mechanical stage 150 (for example—it is rotated about its axis).

System 100 may reduce cross talk while using a single traveling lens acousto-optic device. Cross talk may be achieved by using masking unit 112 that increases the distance between adjacent beams.

Figure 1B:
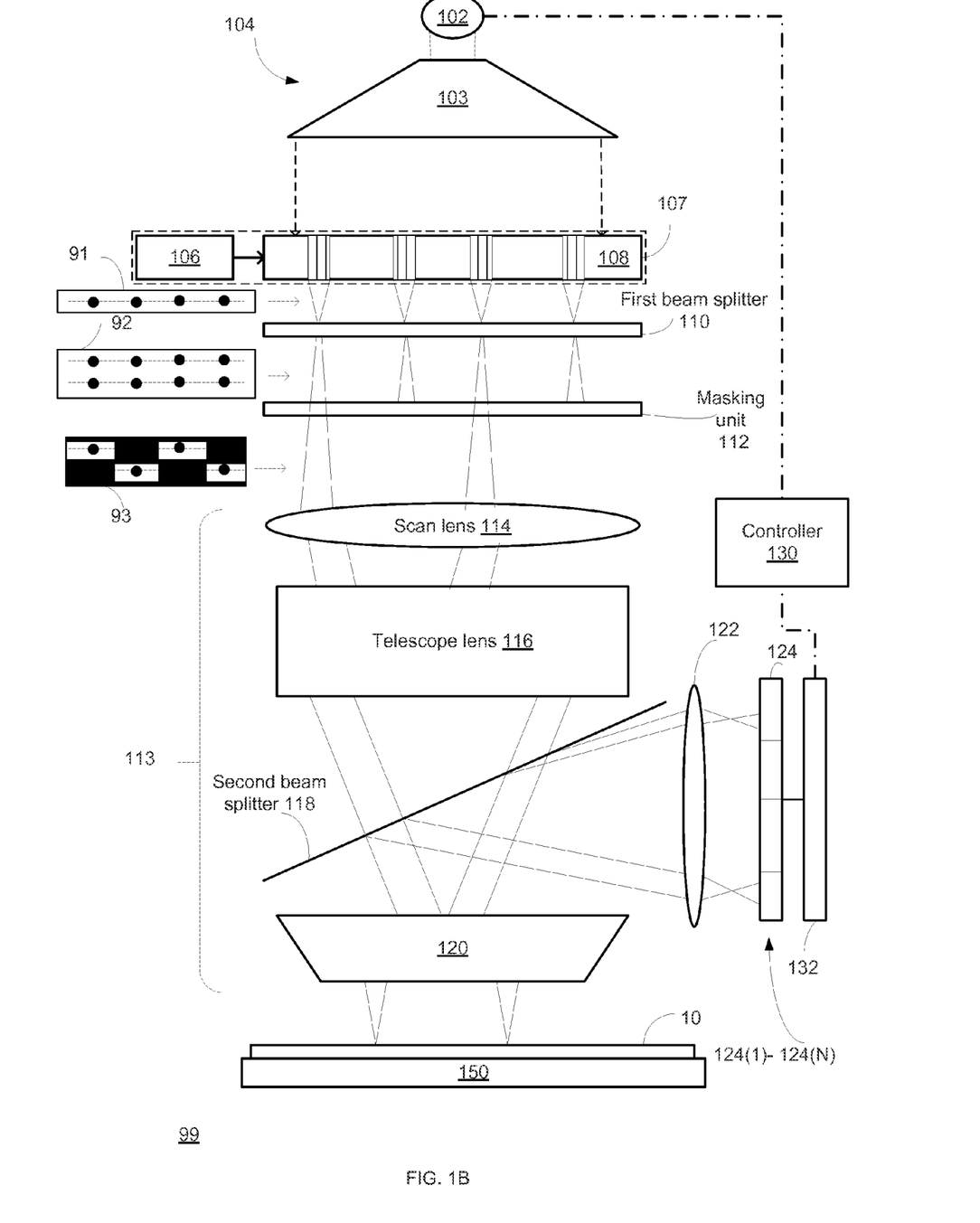
FIG. 1B illustrates a system and an object according to an embodiment of the invention.

FIG. 1B illustrates system 99 and object 10 according to an embodiment of the invention.

In FIG. 1B the optics 113 is illustrated as including scan lens 114, telescope lens 116, output beam splitter 118, objective lens 120 and tube lens 122. Other optical components may form optics 113.

Output beams pass through scan lens 114, telescope lens 116, output beam splitter 118 and objective lens 120 and impinge on object 10.

Collected beams from object 10 pass through objective lens 120, and reflected by output beam splitter 118 towards tube lens 122 and pass through tube lens 122 before impinging on detection unit 124.

Figure 2:
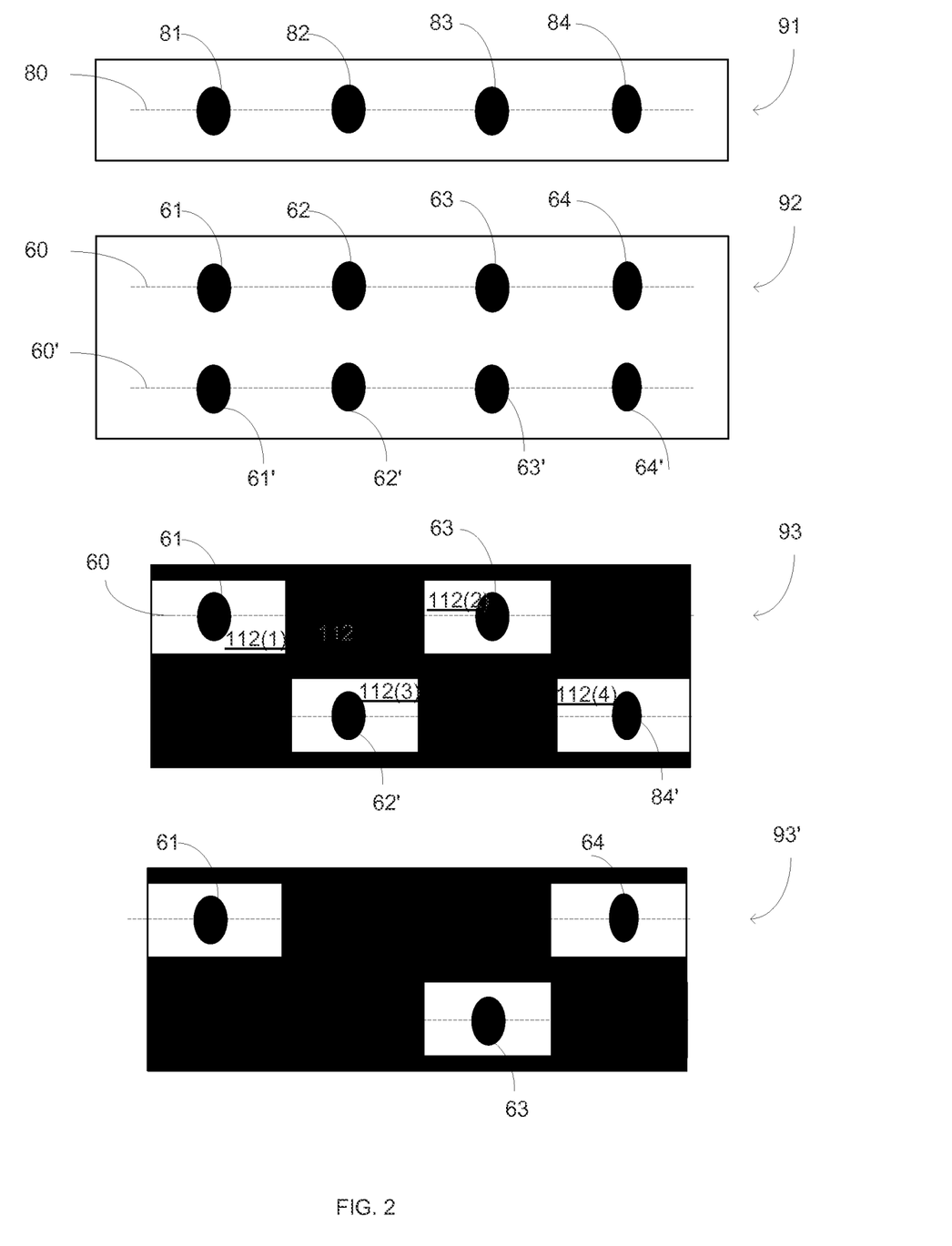
FIG. 2 illustrates beams and masking units according to various embodiments of the invention.

FIG. 2 illustrates beams and masking units according to various embodiments of the invention.

Box 91 illustrates a sequence of input beams that includes input beams 81, 82, 83 and 84 that are spaced apart from each other and propagate along scan axis 80.

Intermediate array 92 includes two intermediate sequences that are parallel to each other and each intermediate sequence includes four intermediate beams—the first intermediate sequence include intermediate beams 61, 62, 63 and 64 while the second intermediate sequence include intermediate beams 61', 62', 63' and 64'.

The intermediate beams of the first intermediate sequence propagate along scan axis 60. The intermediate beams of the second intermediate sequence propagate along scan axis 60'.

Scan axis 60, scan axis 60' and scan axis 80 may be parallel to each other but this is not necessarily so.

The distance between different adjacent intermediate beams may be the same but this is not necessarily so.

The distance between adjacent intermediate beams of the same intermediate sequence (for example—between intermediate beams 61 and 62) may equal to the distance between two intermediate beams (for example—intermediate beams 61 and 61') that belong to different intermediate sequences.

Alternatively—the distance between adjacent intermediate beams of the same intermediate sequence (for example—between intermediate beams 61 and 62) may differ from the distance between a two intermediate beams (for example—intermediate beams 61 and 61') that belong to different intermediate sequences.

Box 93 illustrates a first configuration of masking unit 112 and output beams that propagate through apertures of the masking unit 112. Masking unit 112 masks some of the beams of the first sequence of the intermediate beams and masks some of the beams of the second sequence of the intermediate beams. Intermediate beams 61, 63, 62' and 64' are not output beams that propagate through apertures 112(1), 112(2), 112(3) and 112(4) respectively. Apertures 112(1), 112(2), 112(3) and 112(4) are shaped and sized so that the output beams may follow a predefined scan pattern without being masked. The first configuration of masking unit 112 masks half of the intermediate beams.

The unmasked areas in the masking unit 112 may be configured typically with a small overlap in the scan line direction. This enables a full coverage of the inspected sample It is noted that the separation between the beams in the intermediate sequences may be larger than the separation between the masked areas. Controlling the spacing between the beams can be used to farther decrease the cross talk.

Box 93' illustrates a second configuration of masking unit 112 and output beams that propagate through apertures of the masking unit 112. Masking unit 112 masks two intermediate beams per each unmasked output beam. The second and third intermediate beams 62 and 63 of the first intermediate sequence are masked while first and fourth intermediate beams 61 and 64 are unmasked. The first, second and fourth intermediate beams 61', 62' and 64' of the second intermediate sequence are masked while the third intermediate beam 63' is unmasked. It is assumed that a sixth intermediate beam (if such exists) of the second intermediate sequence is unmasked.

Figure 3A:
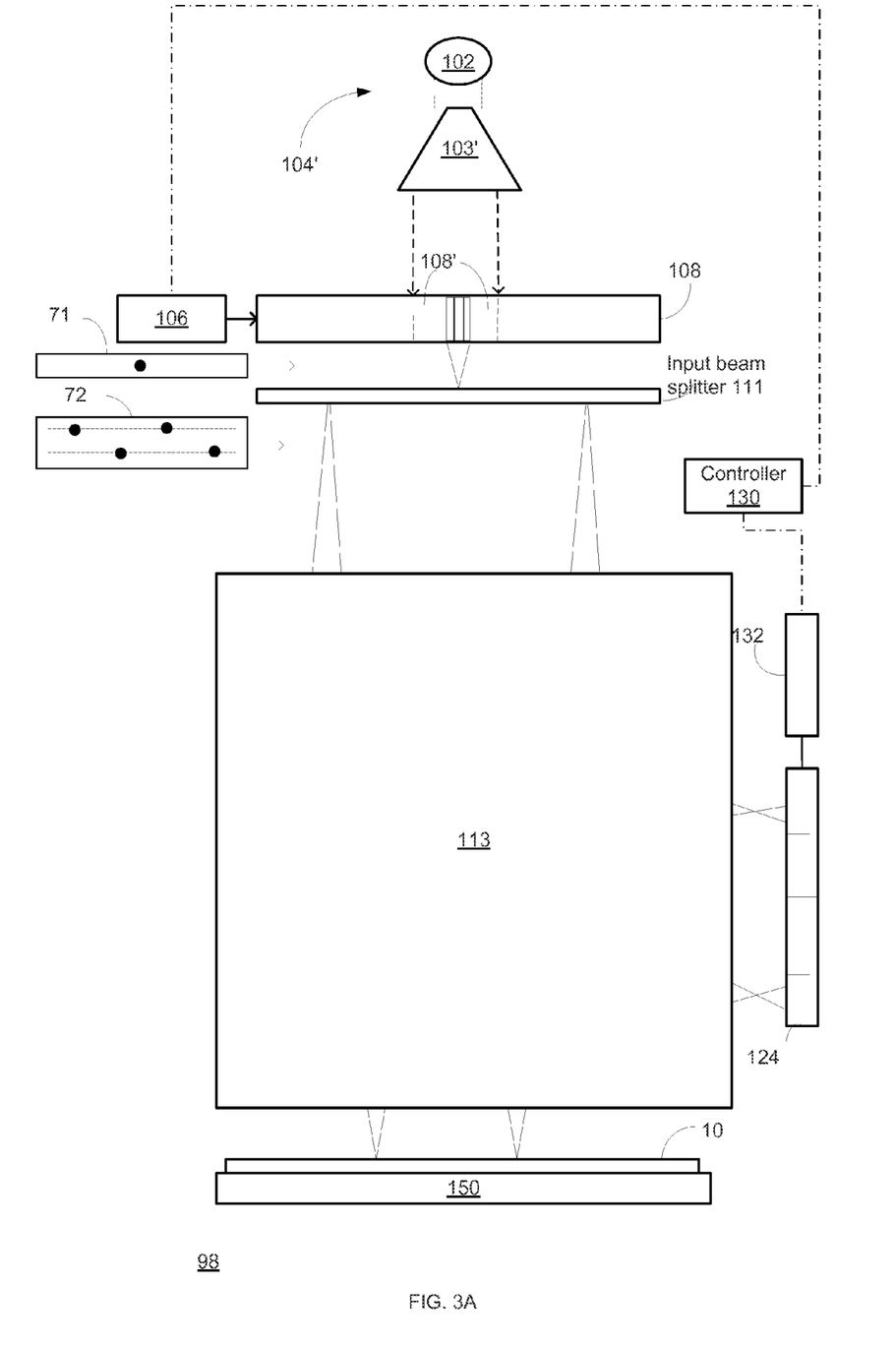
FIG. 3A illustrates a system and an object according to an embodiment of the invention.

FIG. 3A illustrates system 98 according to an embodiment of the invention.

System 98 is illustrated as including: (a) illumination unit 104' that includes light source 102 and beam expander 103' for expanding light from the light source 102, (b) traveling lens acousto-optic device 107 that includes transducer 106 and acousto-optic Bragg cell (hereinafter—Bragg Cell) 108 that acts as the active region of the traveling lens acousto-optic device, (c) input beam splitter 111, (d) optics 113, (e) detection unit 124 that includes a plurality of detectors 124(1)-124(N), N being a positive integer, (f) image processor 132, (g) controller 130, and (h) a mechanical stage 150 for supporting and moving object 10.

Illumination unit 104' illuminates a selected region 108' of Bragg cell 108. Selected region 108' may be smaller than the predefined part illuminated by illumination unit 104 of FIG. 1A. The predefined region 108' should be large enough to enable a single beam generated by a single traveling lens within the Bragg cell to complete a predefined scan pattern. The selected region 108' may be exhibit a uniform intensity profile.

Traveling lens acousto-optic device 107 is configured to generate a single traveling lens that propagates through Bragg cell 108. It is noted that once a travelling lens completes a predefined scan (and illumination iteration is completed) a new traveling lens is generated. Box 71 illustrates a single beam that exits Bragg cell 108.

During each illumination iteration there is a time period during which the entire chirp (and hence the entire traveling lens) propagates through the selected region 108'. During this period detection signals generated by detection unit 124 are deemed to be relevant. Detection signals generated during other time periods may be deemed to be irrelevant.

If the propagation speed of the radio frequency chirp is v, the length of the selected region 108' is Lr and the length of the RF chirp is Lf then the duration of the time period is (Lr−Lf/v). While the entire selected region 108' is illuminated only the light that illuminates the radio frequency chirp is outputted to the object. The illumination efficiency of the configuration of FIG. 3A is (Lr−Lc)*Lr/Lc*Lc. A ratio of Lr/Lc of about 2 may provide adequate performance. Other ratios may be used.

The single beam propagates towards input beam splitter 111 that split the input beam to an output array of output beams that includes rows of output beams and columns of output beams. The output beams propagate along an output scan axis (see scan axis 50 and scan axis 50' of FIG. 4) that is oriented to the columns of the output beams. FIG. 3A includes box 72 that illustrates four beams that propagate along tw0o parallel scan axes.

Figure 4:
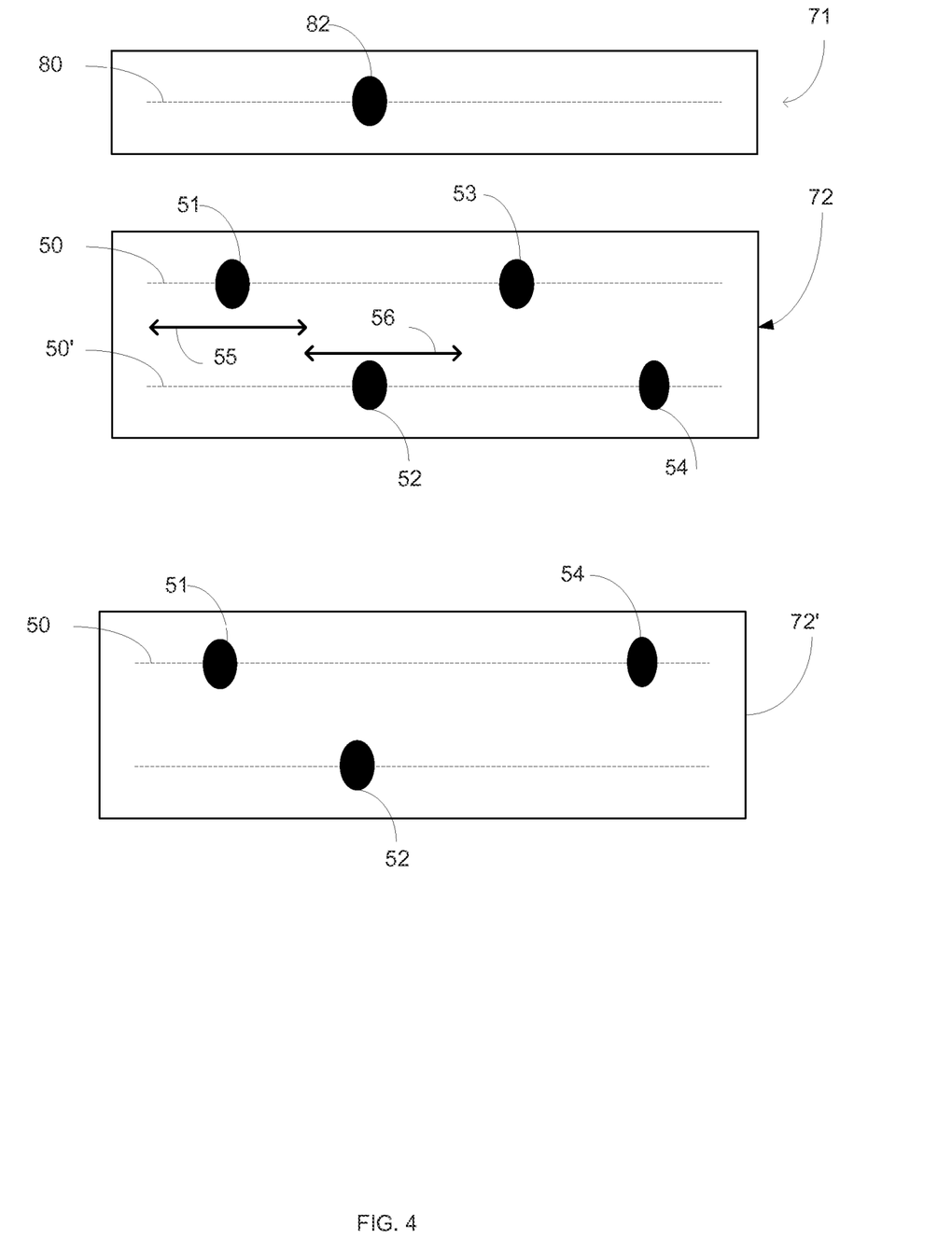
FIG. 4 illustrates beams and masking units according to various embodiments of the invention.

Referring to FIG. 4—output beam 51 scans along scan axis 50 (along a path the is delimited by arrow 55), output beam 52 scans along scan axis 50' (along a path the is delimited by arrow 56). Scan axis 50 and scan axis 50' are oriented to a column of output array that includes output beams 51 and 52.

Referring back to FIG. 3A—optics 113 receive the output beams, direct the output beams towards multiple areas of the object 10, receive collected beams from the multiple areas of the object, and direct the collected beams towards the multiple detectors of detection unit 124. Each detector is associated with an area of the multiple areas.

Multiple detectors of detection unit 124 detect light from the multiple illuminated areas of object 10. They generate detection signals that can be stored and later on processed (for example by image processor 132) in order to detect defects.

Figure 3B:
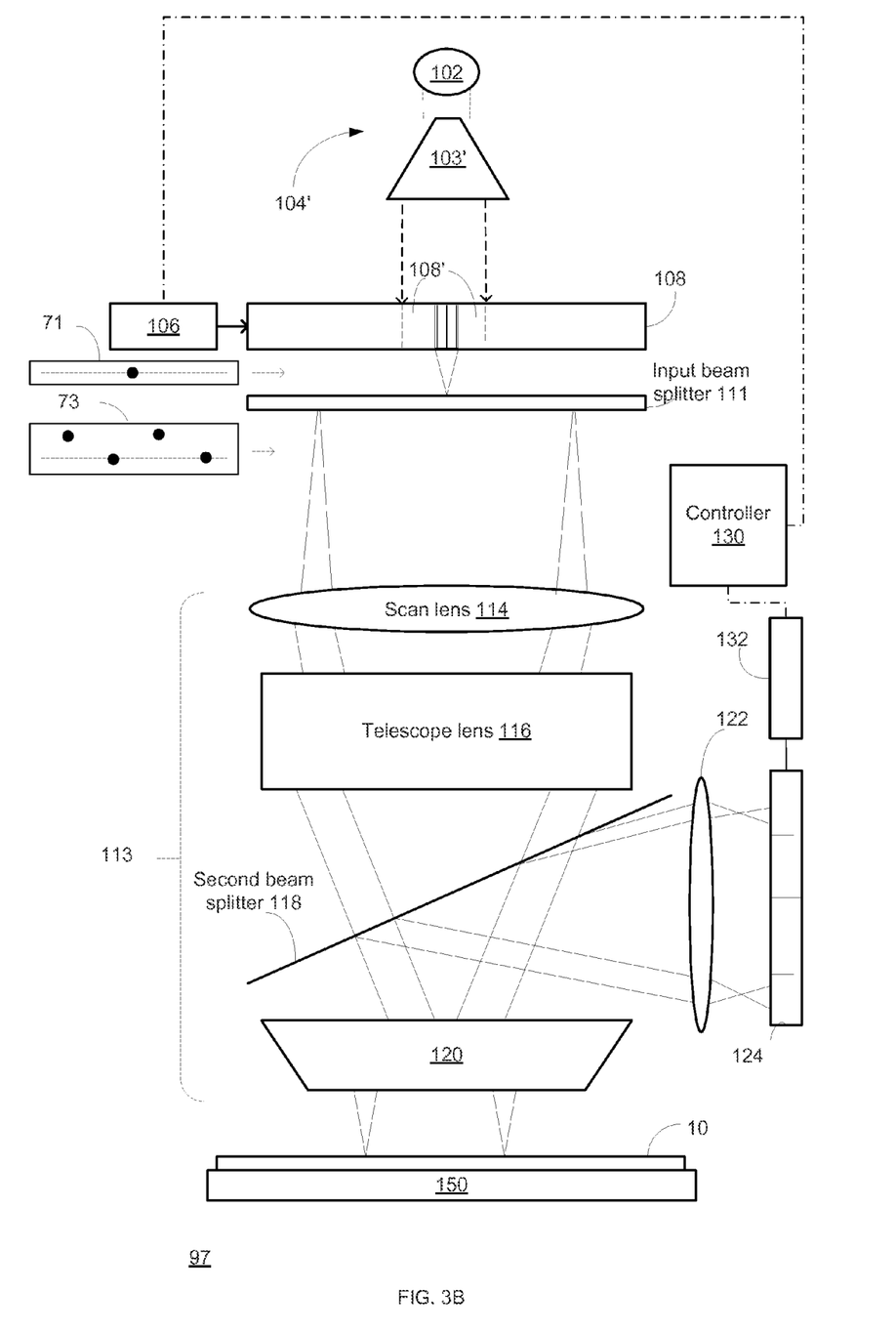
FIG. 3B illustrates a system and an object according to an embodiment of the invention.

FIG. 3B illustrates system 97 and object 10 according to an embodiment of the invention.

In FIG. 3B the optics 113 is illustrated as including scan lens 114, telescope lens 116, output beam splitter 118, objective lens 120 and tube lens 122. Other optical components may form optics 113.

Output beams pass through scan lens 114, telescope lens 116, output beam splitter 118 and objective lens 120 and impinge on object 10.

Collected beams from object 10 pass through objective lens 120, and reflected by output beam splitter 118 towards tube lens 122 and pass through tube lens 122 before impinging on detection unit 124.

Figure 3C:
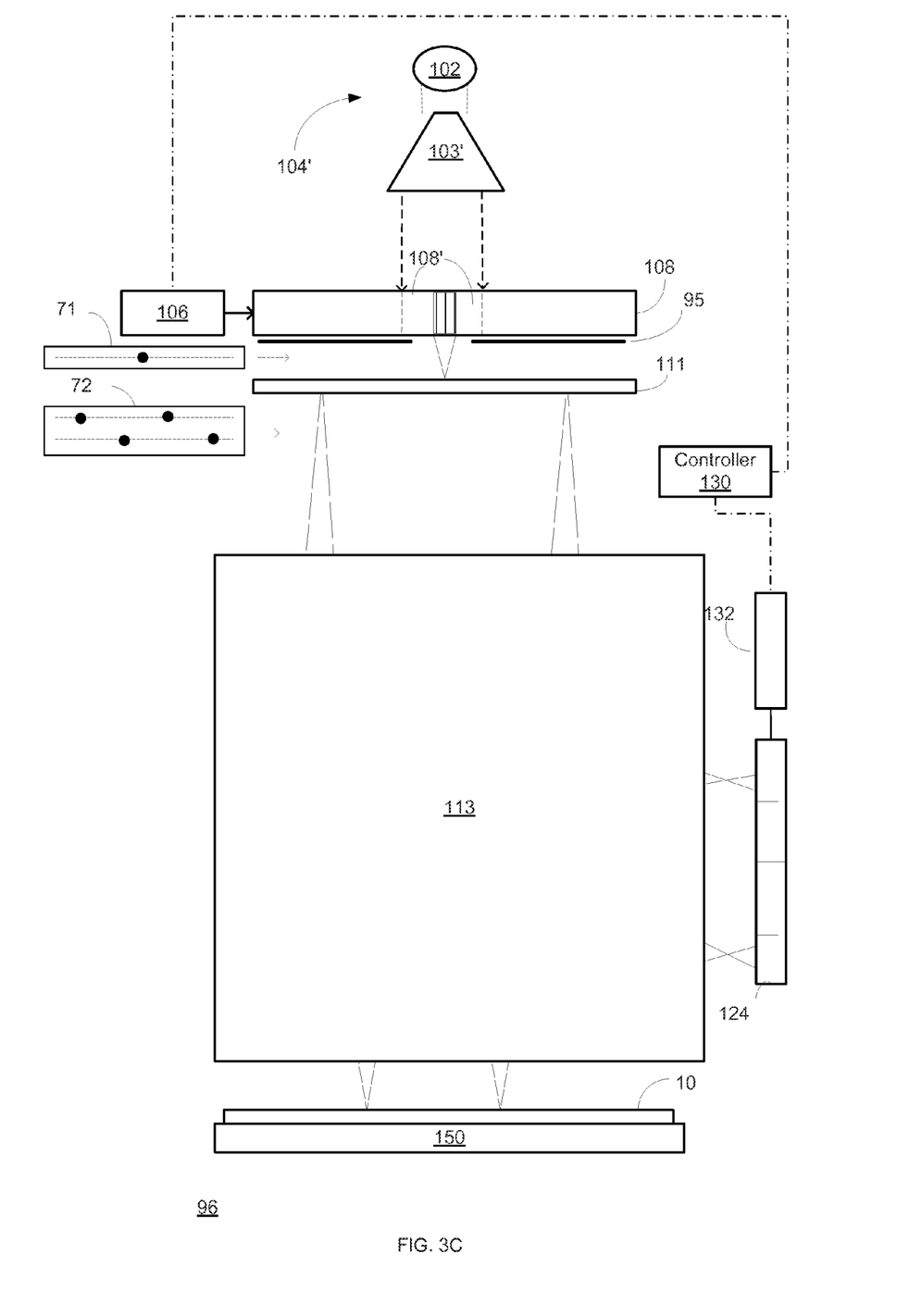
FIG. 3C illustrates a system and an object according to an embodiment of the invention.

FIG. 3C illustrates system 96 and object 10 according to an embodiment of the invention.

In FIG. 3C the optics 113 is illustrated as including scan lens 114, mask 95, telescope lens 116, output beam splitter 118, objective lens 120 and tube lens 122. Other optical components may form optics 113.

Output beams pass through scan lens 114, telescope lens 116, output beam splitter 118 and objective lens 120 and impinge on object 10.

Collected beams from object 10 pass through objective lens 120, and reflected by output beam splitter 118 towards tube lens 122 and pass through tube lens 122 before impinging on detection unit 124.

The scanning of the selected region 108' of Bragg cell 108 by the traveling lens includes three phases. At the beginning of the first phase the traveling lens starts to enter selected region 108'. The first phase ends (and the second phase begins) at the first time the entire traveling lens is within the selected region 108'. The second phase ends (and the third phase begins) at the first time that the traveling lens starts to exit selected region 108'. During the first and third phases only a part of the traveling lens is illuminated and the energy of the beam is less than its maximal level. Only during the second phase the entire traveling lens is illuminated and the beam reaches its maximal level.

According to an embodiment of the invention mask 95 masks the traveling lens outside a portion of the selected region 108' that corresponds to the second phase.

Illumination unit 104' illuminates a selected region 108' of Bragg cell 108. Selected region 108' may be smaller than the predefined part illuminated by illumination unit 104 of FIG. 1A. The predefined region 108' should be large enough to enable a single beam generated by a single traveling lens within the Bragg cell to complete a predefined scan pattern.

FIG. 4 illustrates input beam, and two output arrays of output beams according to various embodiments of the invention.

Box 71 illustrates input beam 82 that propagates along scan axis 80.

Box 72 illustrates an output array of four output beams 51, 52, 53 and 54. Output beams 51 and 53 propagate along scan axis 50. Output beams 52 and 54 propagate along scan axis 50'. Scan axis 50 and scan axis 50' are parallel to each other and spaced apart from each other.

Box 72' illustrates an output array of three output beams 51, 52 and 54. Output beams 51 and 54 propagate along scan axis 50. Output beam 52 propagates along scan axis 50'. Scan axis 50 and scan axis 50' are parallel to each other and spaced apart from each other.

Box 72 and box 72' illustrate diagonal output arrays that differ from each other by the distance between adjacent output beams that propagate along the same scan axis.

Figure 5:
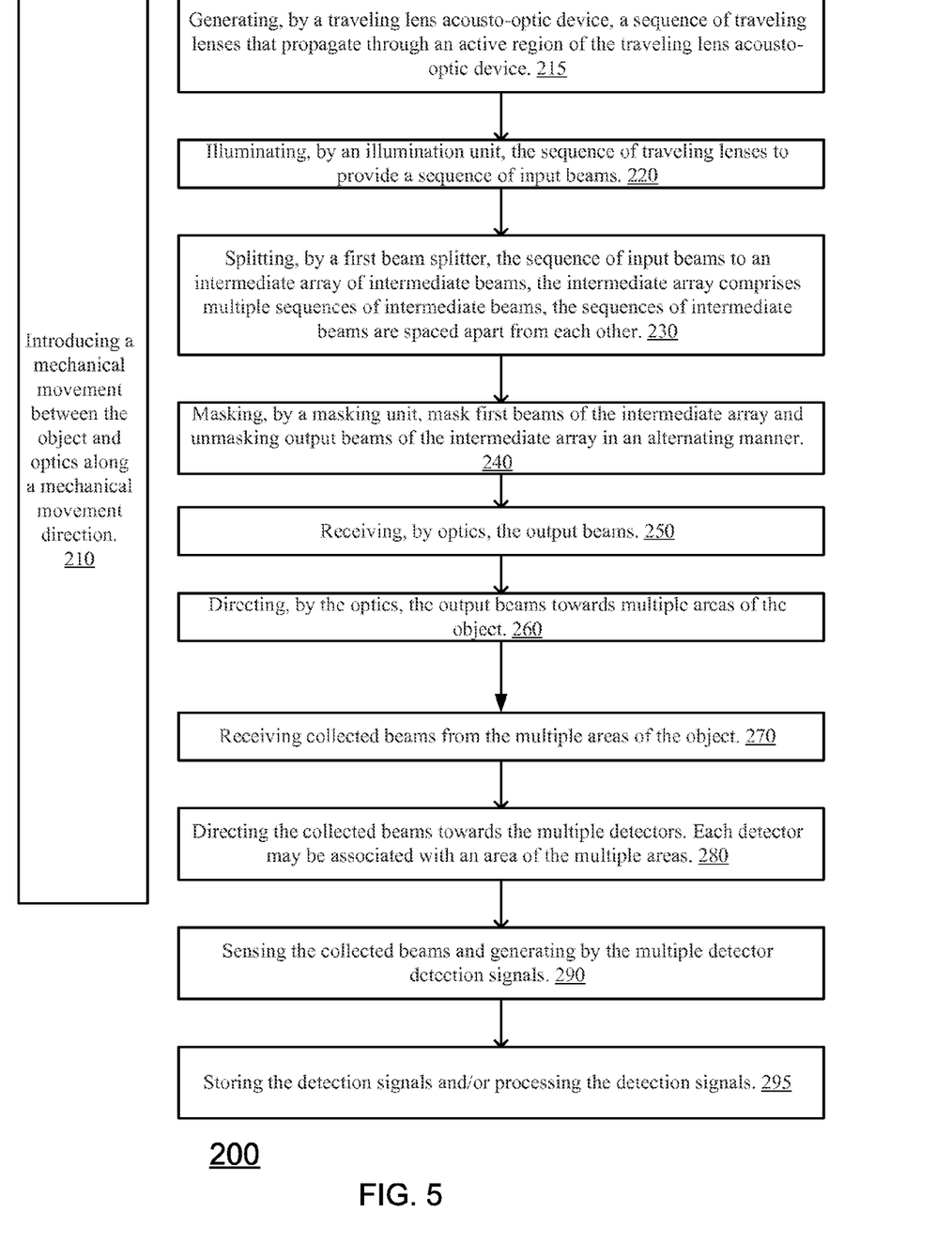
FIG. 5 illustrates a method according to an embodiment of the invention.
Figure 6:
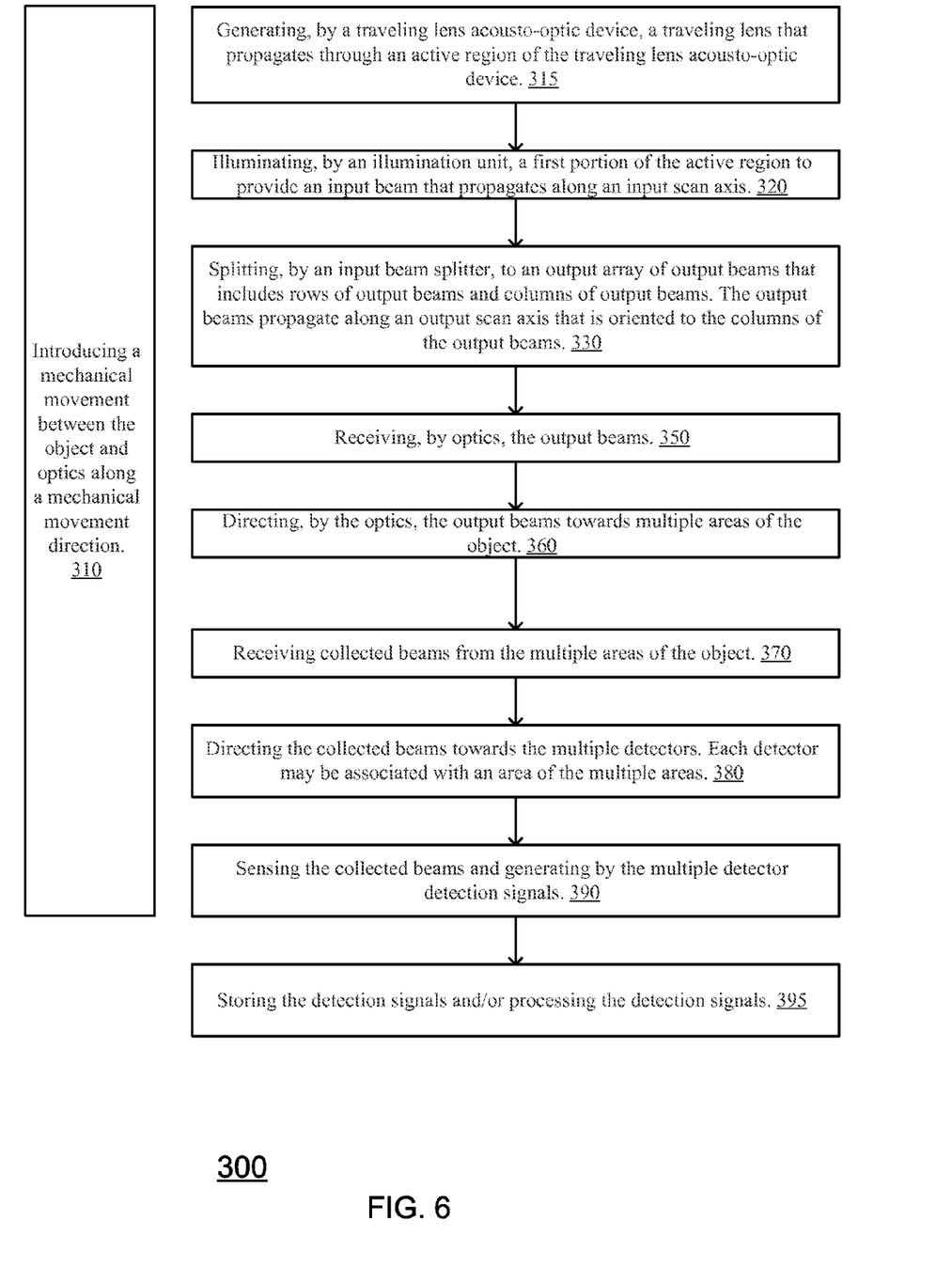
FIG. 6 illustrates a method according to an embodiment of the invention.

FIG. 5 is a flow chart illustrating method 200 for inspecting an object according to an embodiment of the present invention.

Method 200 may be executed by system 100 of FIG. 1A and by system 99 of FIG. 1B.

It is noted that various stages of method 200 at least partially overlap and that their order as illustrated in FIG. 5 is not mandatory.

Method 200 may start by steps 210 and 215.

Step 210 may include introducing a mechanical movement between the object and optics along a mechanical movement direction. Step 210 may be executed in parallel to steps 215, 220, 230, 240, 250, 260, 270 and 280.

Step 215 may include generating, by a traveling lens acousto-optic device, a sequence of traveling lenses that propagate through an active region of the traveling lens acousto-optic device.

Step 210 may be followed by step 220 of illuminating, by an illumination unit, the sequence of traveling lenses to provide a sequence of input beams.

Step 220 may be followed by step 230 of splitting, by a first beam splitter, the sequence of input beams to an intermediate array of intermediate beams, the intermediate array comprises multiple sequences of intermediate beams, the sequences of intermediate beams are spaced apart from each other.

Step 230 may be followed by step 240 of masking, by a masking unit, mask first beams of the intermediate array and unmasking output beams of the intermediate array in an alternating manner.

Step 240 may be followed by step 250 of receiving, by optics, the output beams.

Step 250 may be followed by step 260 of directing, by the optics, the output beams towards multiple areas of the object.

Step 260 may be followed by step 270 of receiving collected beams from the multiple areas of the object.

Step 270 may be followed by step 280 of directing the collected beams towards the multiple detectors. Each detector may be associated with an area of the multiple areas.

Step 280 may be followed by step 290 of sensing the collected beams and generating by the multiple detector detection signals.

Step 290 may be followed by step 295 of storing the detection signals and/or processing the detection signals.

FIG. 5 is a flow chart illustrating method 300 for inspecting an object according to an embodiment of the present invention.

Method 300 may be executed by system 100 of FIG. 1A and by system 99 of FIG. 1B.

It is noted that various stages of method 300 at least partially overlap and that their order as illustrated in FIG. 5 is not mandatory.

Method 300 may start by steps 310 and 315.

Step 310 may include introducing a mechanical movement between the object and optics along a mechanical movement direction. Step 310 may be executed in parallel to steps 315, 320, 330, 350, 360, 370 and 380.

Step 315 may include generating, by a traveling lens acousto-optic device, a traveling lens that propagates through an active region of the traveling lens acousto-optic device.

Step 310 may be followed by step 320 of illuminating, by an illumination unit, a first portion of the active region to provide an input beam that propagates along an input scan axis.

Step 320 may be followed by step 330 of splitting, by an input beam splitter, to an output array of output beams that includes rows of output beams and columns of output beams. The output beams propagate along an output scan axis that is oriented to the columns of the output beams.

Step 330 may be followed by step 350 of receiving, by optics, the output beams.

Step 350 may be followed by step 360 of directing, by the optics, the output beams towards multiple areas of the object.

Step 360 may be followed by step 370 of receiving collected beams from the multiple areas of the object.

Step 370 may be followed by step 380 of directing the collected beams towards the multiple detectors. Each detector may be associated with an area of the multiple areas.

Step 380 may be followed by step 390 of sensing the collected beams and generating by the multiple detector detection signals.

Step 390 may be followed by step 395 of storing the detection signals and/or processing the detection signals.

In the foregoing specification, the invention has been described with reference to specific examples of embodiments of the invention. It will, however, be evident that various modifications and changes may be made therein without departing from the broader spirit and scope of the invention as set forth in the appended claims.

Moreover, the terms "front," "back," "top," "bottom," "over," "under" and the like in the description and in the claims, if any, are used for descriptive purposes and not necessarily for describing permanent relative positions. It is understood that the terms so used are interchangeable under appropriate circumstances such that the embodiments of the invention described herein are, for example, capable of operation in other orientations than those illustrated or otherwise described herein.

The connections as discussed herein may be any type of connection suitable to transfer signals from or to the respective nodes, units or devices, for example via intermediate devices. Accordingly, unless implied or stated otherwise, the connections may for example be direct connections or indirect connections. The connections may be illustrated or described in reference to being a single connection, a plurality of connections, unidirectional connections, or bidirectional connections. However, different embodiments may vary the implementation of the connections. For example, separate unidirectional connections may be used rather than bidirectional connections and vice versa. Also, plurality of connections may be replaced with a single connection that transfers multiple signals serially or in a time multiplexed manner. Likewise, single connections carrying multiple signals may be separated out into various different connections carrying subsets of these signals. Therefore, many options exist for transferring signals.

Although specific conductivity types or polarity of potentials have been described in the examples, it will be appreciated that conductivity types and polarities of potentials may be reversed.

Each signal described herein may be designed as positive or negative logic. In the case of a negative logic signal, the signal is active low where the logically true state corresponds to a logic level zero. In the case of a positive logic signal, the signal is active high where the logically true state corresponds to a logic level one. Note that any of the signals described herein may be designed as either negative or positive logic signals. Therefore, in alternate embodiments, those signals described as positive logic signals may be implemented as negative logic signals, and those signals described as negative logic signals may be implemented as positive logic signals.

Furthermore, the terms "assert" or "set" and "negate" (or "deassert" or "clear") are used herein when referring to the rendering of a signal, status bit, or similar apparatus into its logically true or logically false state, respectively. If the logically true state is a logic level one, the logically false state is a logic level zero. And if the logically true state is a logic level zero, the logically false state is a logic level one.

Those skilled in the art will recognize that the boundaries between logic blocks are merely illustrative and that alternative embodiments may merge logic blocks or circuit elements or impose an alternate decomposition of functionality upon various logic blocks or circuit elements. Thus, it is to be understood that the architectures depicted herein are merely exemplary, and that in fact many other architectures may be implemented which achieve the same functionality.

Any arrangement of components to achieve the same functionality is effectively "associated" such that the desired functionality is achieved. Hence, any two components herein combined to achieve a particular functionality may be seen as "associated with" each other such that the desired functionality is achieved, irrespective of architectures or intermedial components. Likewise, any two components so associated can also be viewed as being "operably connected," or "operably coupled," to each other to achieve the desired functionality.

Furthermore, those skilled in the art will recognize that boundaries between the above described operations merely illustrative. The multiple operations may be combined into a single operation, a single operation may be distributed in additional operations and operations may be executed at least partially overlapping in time. Moreover, alternative embodiments may include multiple instances of a particular operation, and the order of operations may be altered in various other embodiments.

Also for example, in one embodiment, the illustrated examples may be implemented as circuitry located on a single integrated circuit or within a same device. Alternatively, the examples may be implemented as any number of separate integrated circuits or separate devices interconnected with each other in a suitable manner.

However, other modifications, variations and alternatives are also possible. The specifications and drawings are, accordingly, to be regarded in an illustrative rather than in a restrictive sense.

In the claims, any reference signs placed between parentheses shall not be construed as limiting the claim. The word 'comprising' does not exclude the presence of other elements or steps then those listed in a claim. Furthermore, the terms "a" or "an," as used herein, are defined as one or more than one. Also, the use of introductory phrases such as "at least one" and "one or more" in the claims should not be construed to imply that the introduction of another claim element by the indefinite articles "a" or "an" limits any particular claim containing such introduced claim element to inventions containing only one such element, even when the same claim includes the introductory phrases "one or more" or "at least one" and indefinite articles such as "a" or "an." The same holds true for the use of definite articles. Unless stated otherwise, terms such as "first" and "second" are used to arbitrarily distinguish between the elements such terms describe. Thus, these terms are not necessarily intended to indicate temporal or other prioritization of such elements. The mere fact that certain measures are recited in mutually different claims does not indicate that a combination of these measures cannot be used to advantage.

While certain features of the invention have been illustrated and described herein, many modifications, substitutions, changes, and equivalents will now occur to those of ordinary skill in the art. It is, therefore, to be understood that the appended claims are intended to cover all such modifications and changes as fall within the true spirit of the invention.

What is claimed is:

1. A system for inspecting an object, the system comprising:
    a traveling lens acousto-optic device that is configured to generate a sequence of traveling lenses that propagates through an active region of the traveling lens acousto-optic device;
    an illumination unit that is configured to illuminate the sequence of traveling lenses to provide a sequence of input beams;
    a first beam splitter that is configured to split the sequence of input beams to an intermediate array of intermediate beams, the intermediate array comprises multiple sequences of intermediate beams, wherein the intermediate beams in each sequence of intermediate beams are spaced apart from each other, and the multiple sequences of intermediate beams are spaced apart from each other;
    a masking unit having regions for blocking some of the intermediate beams in each sequence of intermediate beams and apertures for allowing some of the intermediate beams in each sequence to pass through, each aperture being shaped and sized to be wider than a width of an intermediate beam to allow the intermediate beam to follow a predefined scan pattern and propagate from one side of the aperture to another side of the aperture without being blocked, the masking unit configured to mask first beams of the intermediate array and unmask output beams of the intermediate array in an alternating manner according to a masking pattern, so that for each sequence of intermediate beams, the masking pattern does not mask adjacent intermediate beams in the sequence or unmask adjacent output beams in the sequence, and wherein for adjacent sequences of the intermediate beams, the masking pattern does not mask adjacent intermediate beams in the adjacent sequences or unmask adjacent output beams in the adjacent sequences;
    a plurality of detectors; and
    optics that are configured to receive the output beams, direct the output beams towards multiple areas of the object, receive collected beams from the multiple areas of the object, and direct the collected beams towards the plurality of detectors;
    wherein each detector in the plurality of detectors is associated with an area of the multiple areas.

2. The system according to claim 1 wherein the output beams form a second array that is oriented in relation to the intermediate array.

3. The system according to claim 1 wherein a number of the first beams is one half of a number of the intermediate beams of the intermediate array.

4. The system according to claim 1 wherein a number of the first beams exceeds one half of a number of the intermediate beams of the intermediate array.

5. The system according to claim 1 wherein the apertures of the masking unit are arranged in a diagonal manner.

6. The system according to claim 1 wherein at least two sequences of intermediate beams of the multiple sequences of intermediate beams are parallel to each other.

7. The system according to claim 1 wherein at least two sequences of intermediate beams of the multiple sequences of intermediate beams are not parallel to each other.

8. A method for inspecting an object, the method comprising:
    generating, by a traveling lens acousto-optic device, a sequence of traveling lenses that propagates through an active region of the traveling lens acousto-optic device;
    illuminating, by an illumination unit, the sequence of traveling lenses to provide a sequence of input beams;
    splitting, by a first beam splitter, the sequence of input beams to an intermediate array of intermediate beams, the intermediate array comprises multiple sequences of intermediate beams, wherein the intermediate beams in each sequence of intermediate beams are spaced apart from each other, and the multiple sequences of intermediate beams are spaced apart from each other;
    masking, by a masking unit having regions for blocking some of the intermediate beams in each sequence of intermediate beams and apertures for allowing some of the intermediate beams in each sequence to pass through, first beams of the intermediate array and unmasking output beams of the intermediate array in an alternating manner according to a masking pattern, so that for each sequence of intermediate beams, the masking pattern does not mask adjacent intermediate beams in the sequence or unmask adjacent output beams in the sequence, and wherein for adjacent sequences of the intermediate beams, the masking pattern does not mask adjacent intermediate beams in the adjacent sequences or unmask adjacent output beams in the adjacent sequences, wherein each aperture of the masking unit is shaped and sized to be wider than a width of an intermediate beam to allow the intermediate beam to follow a predefined scan pattern and propagate from one side of the aperture to another side of the aperture without being blocked;

receiving, by optics, the output beams;

directing, by the optics, the output beams towards multiple areas of the object;

receiving, by the optics, collected beams from the multiple areas of the object; and directing, by the optics, the collected beams towards multiple detectors;

wherein each detector is associated with an area of the multiple areas.

9. The method according to claim 8 wherein the output beams form a second array that is oriented in relation to the intermediate array.

10. A system for inspecting an object, the system comprising:

a traveling lens acousto-optic device adapted to generate a traveling lens that propagates through an active region of the traveling lens acousto-optic device;

an illumination unit that is configured to illuminate a first portion of the active region, the first portion of the active region being wider than a width of the traveling lens, so that when the traveling lens propagates through the first portion, the illumination unit provides an input beam that propagates along an input scan axis;

a mask having an aperture that is substantially aligned with the first portion, the aperture being narrower than a width of the first portion and wider than the width of the traveling lens, wherein the mask is arranged so that the input beam passes through the aperture when the traveling lens propagates through the first potion;

an input beam splitter that is configured to split the input beam passing through the aperture to an output array of output beams that comprises rows of output beams and columns of output beams; wherein the output beams propagate along an output scan axis that is oriented to the columns of the output beams;

a plurality of detectors; and optics that is configured to receive the output beams, direct the output beams towards multiple areas of the object, receive collected beams from the multiple areas of the object, and direct the collected beams towards the plurality of detectors;

wherein each detector in the plurality of detectors is associated with an area of the multiple areas.

11. The system according to claim 10 wherein the output scan axis is oriented by forty five degrees in relation to the columns of the output beams.

12. The system according to claim 10 wherein the output scan axis is oriented by an angle that differs from forty five degrees in relation to the columns of the output beams.

13. The system according to claim 10 wherein a number of the rows of output beams differs from a number of the columns of output beams.

14. The system according to claim 10 wherein a number of the rows of output beams equals a number of the columns of output beams.

* * * * *